United States Patent [19]

Barr

[11] 4,292,028

[45] Sep. 29, 1981

[54] COSMETIC BREATH FRESHENER AND PALATE COOLANT COMPOSITION AND METHOD OF USE

[76] Inventor: Arthur Barr, 2942 Shore Dr., Merrick, N.Y. 11566

[21] Appl. No.: 57,449

[22] Filed: Jul. 13, 1979

[51] Int. Cl.$^3$ .............................................. A61C 13/22
[52] U.S. Cl. ....................................... 433/180; 424/19; 106/35
[58] Field of Search ........................... 424/19; 433/180; 106/35

[56] References Cited

U.S. PATENT DOCUMENTS

| | | | |
|---|---|---|---|
| 2,574,476 | 11/1951 | Heath et al. | 106/35 X |
| 2,701,212 | 2/1955 | Brennan | 424/58 X |
| 3,029,187 | 4/1962 | Steinhardt | 433/180 X |
| 3,029,188 | 4/1962 | Cyr et al. | 433/180 X |
| 3,886,265 | 5/1975 | Evers et al. | 424/49 |
| 3,969,499 | 7/1976 | Lee, Jr. et al. | 424/52 |
| 4,029,759 | 6/1977 | Humbert et al. | 424/16 X |
| 4,039,653 | 8/1977 | DeFoney et al. | 424/19 |
| 4,071,614 | 1/1978 | Grimm | 424/49 |

*Primary Examiner*—Joseph Paul Brust
*Attorney, Agent, or Firm*—Hane, Roberts, Spiecens & Cohen

[57] ABSTRACT

A cosmetic breath freshener composition having slow release comprising a multiplicity of microencapsulated liquid droplets of flavoring material contained in a carrier. The microencapsulated droplets are soluble in the saliva in the mouth to release the flavoring material. The composition can be used in conjunction with a dental adhesive particularly for use with dentures to release the flavoring material at a sustained rate for long periods of time in the mouth to mask bad breath.

2 Claims, No Drawings

COSMETIC BREATH FRESHENER AND PALATE COOLANT COMPOSITION AND METHOD OF USE

FIELD OF THE INVENTION

The invention relates to a breath freshener composition capable of slow release, at a sustained rate, of a microencapsulated liquid flavoring material and to methods of use thereof.

The invention is particularly applicable to the use of such a breath freshener composition for full or partial denture wearers but is also applicable to the use of non-denture wearers and hence to the general public.

BACKGROUND

One of the major problems involved in the use of full or partial dentures is the production of offensive denture breath, or "bad breath" due to food and beverage retained between the palate and denture, and the capturing of food in denture adhesive, used by some denture wearers.

Up to the present no satisfactory compositions or methods have been obtained which will overcome this problem for long periods of time, and despite the widespread use of varying dental flavoring materials there has been no effective long-term solution to overcome the problem of offensive denture breadth (bad breath).

Indeed, such problem makes difficult the patient's transition to the wearing of dentures. Flavorings, such as spray breath fresheners, mouth washes, chewing gums, lozenges, and denture cleaners as presently employed have only a limited life of very short duration and rapidly lose their ability to mask bad breath.

SUMMARY OF THE INVENTION

An object of the invention is to provide a breath freshener composition and palate coolant, having slow release in the mouth and capable of eliminating offensive breath and cooling the palate at the same time.

A further object of the invention is to provide such a breath freshener composition adapted specifically for use with full or partial dentures by compatability thereof with or without the use of a denture adhesive.

According to a feature of the invention, the breath freshener composition may be in the form of a paste, cream, or gel adapted for application directly to the inner surfaces of the dentures, or it can be in the form of a wafer having an adhesive coating thereon for adherent contact with the palate or gums of the user.

In accordance with the invention, there is provided a breath freshener composition having slow release comprising a multiplicity of microencapsulated liquid droplets of flavoring material, the microencapsulated droplets being soluble in the saliva of the mouth to slowly release the flavoring material when entering into contact with the saliva. As a consequence, the microencapsulates can slowly release the liquid flavoring material at a sustained rate. The microencapsulates are present in a base which may comprise a dental adhesive. In a modified form, the base is constituted as a wafer having an adhesive coating thereon. In this way, the composition can be applied to the palate or gums of the user independently of the use of dentures, or alternatively, the wafer can be directly applied to the inner surfaces of its dentures.

In accordance with a specific embodiment of the invention, the encapsulated flavoring material is present in an amount of 3-15% by weight of the composition. The base is present as a remainder of 85-97% and comprises petrolatum and karaya gum. The gum can be present in an amount of 51% by weight of the composition and the petrolatum in an amount of 30% by weight of the composition.

PRIOR ART

U.S. Pat. No. 2,701,212 relates to germicidal deodorizing powder adhesives and methods of manufacture thereof. The patent discloses powdered adhesives containing various amounts of finely divided karaya gum and borax with and without water-soluble chlorophyllin. This patent lacks any teaching concerning encapsulated minute droplets of flavoring material having slow release at a sustained rate.

U.S. Pat. No. 3,440,065 relates to an improved denture adhesive containing various additives, such as wood, flour, cellulose or other wood pulp derivatives which are added to a gum-petrolatum base. The patent discloses an adhesive composition of a topically acceptable hydrocolloid, powdered insoluble adsorptive cellulose material and petrolatum. The purpose of the cellulose material is to effect a greater hydration of the gum particles, not only on the surface, but throughout the paste and thereby effect a much stronger cohesive bond between the denture and the gingiva and palate. In addition, a flavoring oil is blended into the composition, but lacking is any teaching regarding sustained time release based on the use of encapsulated flavoring materials.

U.S. Pat. No. 3,886,265 discloses a mouth cleansing preparation containing at least one ene-diol compound having at most 6 carbon atoms and an oxidizing agent in the form of a water soluble peroxide. The composition is intended to eliminate bad breath and is employed in the form of a chewable tablet. The composition can contain flavoring agents, but these are not in the form of encapsulated droplets adapted for slow sustained release in the mouth.

U.S. Pat. No. 3,969,499 discloses dental adhesive materials in the form of plastic films or membranes which are implanted in or adhered to tissue, bone or tooth substrate in which a medicament such as a fluoride compound is imbedded. The medicament is released from the plastic over a period of time. Specifically, the composition is intended for use as a dental fissure sealant. There is no teaching in this reference of a sustained release of flavoring material.

U.S. Pat. No. 4,029,759 discloses a method for imparting a cooling property to a composition for use in the oral cavity. Specifically, the patent discloses the use of para-menthane derivatives to various substances used in the mouth, such as toothpaste, mouthwash, tooth powder, food stuffs and the like. The para-menthane derivatives can also be employed in combination with flavoring materials. Lacking in this disclosure is any teaching concerning sustained slow release of flavoring material in the mouth.

U.S. Pat. No. 4,071,614 discloses a dentifrice which contains encapsulated flavoring materials. The dentifrice contains two different flavoring materials in which one flavor is encapsulated in a thin walled capsule and the other is encapsulated in a thick walled capsule. The thin walled capsules rupture when the toothpaste is squeezed from the container and the thick walled capsules rupture in the course of brushing the teeth. The encapsulated material is not water-soluble and is intended for being broken by a mechanical action to release bursts of the flavoring material. There is thus no disclosure in respect of a slow sustained release of flavoring material, particularly, in conjunction with a static situation, such as, installation of dentures.

DESCRIPTION OF PREFERRED EMBODIMENTS

In order to confer a slow sustained release of flavoring materials into the mouth of a user there is employed a multiplicity of microencapsulated liquid droplets of flavoring material in a prepared base composition. The encapsulated droplets are soluble in the saliva in the mouth of the user so as to dissolve the microcapsulation material and release the flavoring material when entering into contact with saliva in the mouth.

The formation of microencapsulated liquid droplets of material is well known in the art and does not form any part of the present invention. Hence, it will not be described at length herein. However, for the purpose of brief explanation, reference is made to the publication "Microencapsulation" by Herbig as presented in the "Encyclopedia of Chemical Technology" of Kirk-Othmer, Volume 13, 2nd Edition, pp 436-456. As disclosed herein, minute particles or liquid droplets of material can be encased by an impervious capsule wall and isolated from the surrounding atmosphere.

In the circumstances of the present invention, the liquid flavoring material is encapsulated in a non-water soluble coating and the coating may be of varying wall thickness in order to provide for sustained release of the flavoring material over a period of time, of the order of several hours, when the encapsulated droplets come into contact with saliva in the mouth. The encapsulating material must satisfy the purposes of the invention of being saliva-soluble and providing sustained release of the encapsulated flavoring material while being not soluble in water and thus capable of long shelf life without weight loss to the ambient atmosphere. Furthermore, because of this property, breakdown of capsules will not be speeded up by intake of drinking water or other water containing beverages.

The multiplicity of microencapsulated liquid droplets of flavoring material is incorporated into a base and the base may take one of many different forms. In one form, the base is constituted as a cream or gel which can be placed on the inner surfaces of dentures at the time of emplacement thereof to slowly release the flavoring materials over a period of time. In a modification, the cream or gel material can itself contain a denture adhesive so as to be directly usable for emplacement of the dentures. In a further modification, the base incorporating the microcapsulates of liquid droplet can be formed as a wafer having adhesive coating thereon whereby the wafer can be affixed to the palate or gums of the wearer and slowly release the flavoring material. The wafer can be thus utilized whether the user wears dentures or not and will provide protection against "bad breath" for several hours. The length of protection is based upon the amount of product used.

When the base is constituted of a cream or gel material this can be mixed directly with a denture adhesive to serve the purpose of adhering the dentures in place in the mouth while at the same time serving to release the flavoring material over a period of time.

The flavoring material can be of wide range and by way of example it may be a mint flavor such as spearmint, peppermint, oil of wintergreen, etc. Also, useable are fruit flavors or other flavorings such as vanillin. The flavoring material is present in an amount of 3-15% by weight of the composition.

The base which represents the remainder of the composition is present in an amount of 85-97% by weight and serves as the vehicle for containing the encapsulated flavoring material distributed therethroughout.

The base or carrier for the encapsulated flavoring material is in the form of a mixture of a gum in a petrolatum base. Specifically, a gum such as karaya gum in an amount of 51% is mixed with 30% by weight of petrolatum. Additionally contained in the carrier is mineral oil in an amount of about 12%. If it is desired to make the composition of a softer consistency, the petrolatum is reduced in an amount of the order of 1-2% and the amount of mineral oil is increased by this same amount.

The carrier can contain additional substances and these include a small percentage of titanium dioxide as a whitener and a small percentage of propylparaben as an antifungicide.

EXAMPLE

Microencapsulated droplets were prepared by encapsulating peppermint flavoring in liquid droplet form in an encapsulating material which is substantially not soluble in water but is soluble in saliva in the mouth of the user.

A microencapsulated droplet composition prepared according to the invention includes the following components in % by weight.

| | |
|---|---|
| liquid peppermint | 91% |
| gelatin | 4.25% |
| gum arabic | 4.25% |
| glutaraldehyde (gelatin cross-linking agent) | .25% |
| sodium silicate (Aerosil 972) | .25% |

The microencapsulated droplets have a size of between 100 and 300 microns and a wall thickness of less than 5 microns and generally between 2 and 3 microns. The droplets were found to have a maximum weight loss in air of about 10% which was achieved within about 9 days whereafter there was no further weight loss. The microencapsulated droplets were not soluble in water but were slowly soluble in saliva in the mouth of the user.

The following composition of the invention was prepared by the method to be described hereafter.

| INGREDIENT | PERCENT BY WEIGHT |
|---|---|
| Microencapsulated peppermint droplets (as prepared above) | 6 |
| Karaya gum | 51 |
| Petrolatum | 30 |
| Mineral oil | 12.4 |
| Titanium dioxide | 0.5 |
| Propylparaben | 0.1 |

The composition was prepared by first premilling the titanium dioxide in 4.5% by weight of the mineral oil to prepare a 10% dispersion.

The remainder or 7.9% of the mineral oil was added to a jacketed stainless steel kettle equipped with side scraping sweep agitation. To the kettle was then added the propylparaben, the petrolatum and the titanium dioxide dispersion. The mixture was heated to a temperature of 55° C. with agitation.

The karaya gum was then added and mixing was continued until a uniform mixture was obtained. The encapsulated flavoring material was then added and mixing was continued until the encapsulated flavoring material was uniformly distributed throughout the mixture.

The mixture was then transferred at a temperature of 50° C. to a filling station where tubes were filled with the mixture.

In use, the composition was applied to a denture and for this purpose one or two small dabs was found to be sufficient. The denture was then introduced into the mouth of the user and the flavoring material was found to be slowly released in situ in the mouth at a sustained rate. It was found that the composition is effective for long periods of time of the order of 4-10 hours.

For non-denture wearer use, one dab applied to the upper gums adjacent to the cheek was found to provide effective protection against bad breath for periods of time in the order of 4-8 hours.

It was also unexpectedly found that the composition had a cooling effect in the mouth and this is of particular significance when used with dentures where the contact of the dentures in the mouth of the user normally produces an uncomfortable warming effect. This was found to be overcome by the cooling effect of the composition of the invention.

Although the invention has been described in conjunction with a specific embodiment thereof it will be apparent to those skilled in the art that numerous modifications and variations can be undertaken without departing from the scope and spirit of the invention as defined in the attached claims.

What is claimed is:

1. A method of adhesively securing a denture in the mouth of a user while releasing a flavoring material and providing a cooling effect, said method comprising forming a paste composition consisting of microencapsulated droplets of liquid flavoring material in a paste carrier, said microencapsulated droplets being constituted of a coating which is substantially non-soluble in water but is soluble in the saliva of the mouth, said paste carrier being adhesive, applying a quantity of the composition to a denture and introducing the denture into the mouth of a user such that the composition adhesively secures the denture in place in the mouth whereafter the flavoring material is slowly released in situ in the mouth at a sustained rate, the composition of the liquid flavoring material and its encapsulation in the carrier being such as to provide a cooling effect in the mouth of the user as the droplets of material are slowly dissolved and thereby opposing warming effect normally produced by the denture in the mouth, said microencapsulated droplets being present in an amount of 6% by weight and consisting of the following in percent by weight;

| Liquid flavoring material | 91% |
| --- | --- |
| Gelatin | 4.25% |
| Gum arabic | 4.25% |
| Glutaraldehyde | .25% |
| Sodium silicate | .25% | said paste carrier consisting of the following in percent by weight;

| Karaya gum | 51% |
| --- | --- |
| Petrolatum | 30% |
| Propylparaben | 0.1% |
| Mineral oil | 12.4% |
| Titanium dioxide | 0.4% |

2. A method as claimed in claim 1 wherein the flavoring material is a mint flavored material.

* * * * *